United States Patent
Ingimundarson et al.

(10) Patent No.: US 8,939,925 B2
(45) Date of Patent: Jan. 27, 2015

(54) TIGHTENING SYSTEM FOR AN ORTHOPEDIC ARTICLE

(75) Inventors: Arni Thor Ingimundarson, Ladera Ranch, CA (US); Janaki Ram-srinivasaRao Chetlapalli, Irvine, CA (US); Bjorn Omarsson, Reykjavik (IS); Nina Bakken, Oslo (NO)

(73) Assignee: OSSUR HF, Reykjavik (IS)

( * ) Notice: Subject to any disclaimer, the term of this patent is extended or adjusted under 35 U.S.C. 154(b) by 305 days.

(21) Appl. No.: 13/370,512

(22) Filed: Feb. 10, 2012

(65) Prior Publication Data
US 2012/0204381 A1    Aug. 16, 2012

Related U.S. Application Data

(60) Provisional application No. 61/441,588, filed on Feb. 10, 2011.

(51) Int. Cl.
*A61F 5/02* (2006.01)
*A41F 1/04* (2006.01)

(52) U.S. Cl.
CPC .. *A61F 5/028* (2013.01); *A41F 1/04* (2013.01)
USPC ............................................. 602/19; 128/876

(58) Field of Classification Search
CPC ........... A61F 5/02; A61F 5/028; A61F 5/022; A61F 5/024; A61F 5/026; A61F 5/03
USPC ........... 602/5, 16, 19; 24/71.1, 58 SK, 68 SK; 128/876, 100.1, 101.1; 224/162–163
See application file for complete search history.

(56) References Cited

U.S. PATENT DOCUMENTS

| | | | |
|---|---|---|---|
| 3,793,749 A | 2/1974 | Gertsch et al. |
| 3,808,644 A | 5/1974 | Schoch |
| 3,889,664 A | 6/1975 | Heuser et al. |
| 3,926,182 A | 12/1975 | Stabholz |
| 4,261,081 A | 4/1981 | Lott |
| 4,433,456 A | 2/1984 | Baggio |
| 4,551,932 A | 11/1985 | Schoch |

(Continued)

FOREIGN PATENT DOCUMENTS

| | | |
|---|---|---|
| CA | 2112789 A1 | 1/1994 |
| CA | 2114387 A1 | 1/1994 |

(Continued)

OTHER PUBLICATIONS

International Search Report and Written Opinion issued in PCT/2012/024619, May 16, 2012.

*Primary Examiner* — Patricia Bianco
*Assistant Examiner* — Kari Petrik
(74) *Attorney, Agent, or Firm* — Workman Nydegger

(57) ABSTRACT

A tightening system and method for operating the same in an article for a wearer includes first and second members arranged for being connected at first ends, and separated by a distance at second ends. A tension element connects the first and second members. A tensioning mechanism is mounted on the first member and coupled to the tension element. The tensioning mechanism includes a housing and a retractable and extendable line arranged to be extended from the housing and automatically retract to the housing upon release of the line to permit one-way incremental winding of the tension element to thereby draw the first and second members closer to one another by reducing the distance therebetween.

17 Claims, 4 Drawing Sheets

(56) References Cited

U.S. PATENT DOCUMENTS

| | | | |
|---|---|---|---|
| 4,555,830 A | 12/1985 | Petrini et al. |
| 4,574,500 A | 3/1986 | Aldinio et al. |
| 4,616,524 A | 10/1986 | Bidoia |
| 4,619,657 A | 10/1986 | Keates et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,654,985 A | 4/1987 | Chalmers |
| 4,660,300 A | 4/1987 | Morrell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,741,115 A | 5/1988 | Pozzobon |
| 4,748,726 A | 6/1988 | Schoch |
| 4,760,653 A | 8/1988 | Baggio |
| 4,799,297 A | 1/1989 | Baggio et al. |
| 4,802,291 A | 2/1989 | Sartor |
| 4,811,503 A | 3/1989 | Iwama |
| 4,841,649 A | 6/1989 | Baggio et al. |
| 4,884,760 A | 12/1989 | Baggio et al. |
| 4,961,544 A | 10/1990 | Bidoia |
| 5,042,177 A | 8/1991 | Schoch |
| 5,062,225 A | 11/1991 | Gorza |
| 5,065,481 A | 11/1991 | Walkhoff |
| 5,092,321 A | 3/1992 | Spademan |
| 5,117,567 A | 6/1992 | Berger |
| 5,152,038 A | 10/1992 | Schoch |
| 5,157,813 A | 10/1992 | Carroll |
| 5,177,882 A | 1/1993 | Berger |
| 5,181,331 A | 1/1993 | Berger |
| 5,183,036 A | 2/1993 | Spademan |
| 5,249,377 A | 10/1993 | Walkhoff |
| 5,325,613 A | 7/1994 | Sussmann |
| 5,327,662 A | 7/1994 | Hallenbeck |
| 5,365,947 A | 11/1994 | Bonutti |
| 5,433,648 A | 7/1995 | Frydman |
| 5,437,619 A | 8/1995 | Malewicz et al. |
| 5,477,593 A | 12/1995 | Leick |
| 5,502,902 A | 4/1996 | Sussmann |
| 5,599,288 A | 2/1997 | Shirley et al. |
| 5,638,588 A | 6/1997 | Jungkind |
| 5,647,104 A | 7/1997 | James |
| 5,669,116 A | 9/1997 | Jungkind |
| 5,685,830 A | 11/1997 | Bonutti |
| 5,732,483 A | 3/1998 | Cagliari |
| 5,737,854 A | 4/1998 | Sussmann |
| 5,819,378 A | 10/1998 | Doyle |
| 5,848,979 A | 12/1998 | Bonutti et al. |
| 5,891,061 A | 4/1999 | Kaiser |
| 5,934,599 A | 8/1999 | Hammerslag |
| 6,159,248 A | 12/2000 | Grammas |
| 6,190,343 B1 | 2/2001 | Heinz et al. |
| 6,202,953 B1 | 3/2001 | Hammerslag |
| 6,206,932 B1 | 3/2001 | Johnson |
| 6,256,798 B1 | 7/2001 | Egolf et al. |
| 6,267,390 B1 | 7/2001 | Maravetz et al. |
| 6,289,558 B1 | 9/2001 | Hammerslag |
| 6,413,232 B1 | 7/2002 | Townsend et al. |
| 6,416,074 B1 | 7/2002 | Maravetz et al. |
| 6,500,139 B1 | 12/2002 | Townsend et al. |
| 6,502,577 B1 | 1/2003 | Bonutti |
| 6,503,213 B2 | 1/2003 | Bonutti |
| 6,689,080 B2 | 2/2004 | Castillo |
| 6,711,787 B2 | 3/2004 | Jungkind et al. |
| 6,769,155 B2 | 8/2004 | Hess et al. |
| 6,770,047 B2 | 8/2004 | Bonutti |
| 6,827,653 B2 | 12/2004 | Be |
| 6,921,377 B2 | 7/2005 | Bonutti |
| 7,001,348 B2 | 2/2006 | Garth et al. |
| D519,637 S | 4/2006 | Nordt et al. |
| D520,141 S | 5/2006 | Nordt et al. |
| D521,644 S | 5/2006 | Nordt et al. |
| 7,076,843 B2 | 7/2006 | Sakabayashi |
| 7,128,724 B2 | 10/2006 | Marsh |
| 7,134,224 B2 | 11/2006 | Elkington et al. |
| 7,198,610 B2 | 4/2007 | Ingimundarson et al. |
| 7,235,059 B2 | 6/2007 | Mason et al. |
| 7,281,341 B2 | 10/2007 | Reagan et al. |
| 7,306,573 B2 | 12/2007 | Bonutti |
| 7,331,126 B2 | 2/2008 | Johnson |
| 7,402,147 B1 | 7/2008 | Allen |
| 7,404,804 B2 | 7/2008 | Bonutti |
| 7,416,565 B1 | 8/2008 | Al-Turaikl |
| 7,438,698 B2 | 10/2008 | Daiju |
| 7,513,018 B2 | 4/2009 | Koenig et al. |
| 7,591,050 B2 | 9/2009 | Hammerslag |
| 7,597,675 B2 | 10/2009 | Ingimundarson et al. |
| 7,600,660 B2 | 10/2009 | Kasper et al. |
| 7,618,386 B2 | 11/2009 | Nordt, III et al. |
| 7,618,389 B2 | 11/2009 | Nordt, III et al. |
| 7,670,306 B2 | 3/2010 | Nordt, III et al. |
| 7,699,797 B2 | 4/2010 | Nordt, III et al. |
| 7,704,219 B2 | 4/2010 | Nordt, III et al. |
| 7,806,842 B2 | 10/2010 | Stevenson et al. |
| 7,857,776 B2 | 12/2010 | Frisbie |
| 7,862,621 B2 | 1/2011 | Kloos et al. |
| 7,878,998 B2 | 2/2011 | Nordt, III et al. |
| 7,887,500 B2 | 2/2011 | Nordt, III et al. |
| 7,922,680 B2 | 4/2011 | Nordt, III et al. |
| 7,950,112 B2 | 5/2011 | Hammerslag et al. |
| 7,954,204 B2 | 6/2011 | Hammerslag et al. |
| 7,993,296 B2 | 8/2011 | Nordt, III et al. |
| 8,002,724 B2 | 8/2011 | Hu et al. |
| 8,038,635 B2 | 10/2011 | Dellanno |
| 8,038,637 B2 | 10/2011 | Bonutti |
| 8,079,433 B2 | 12/2011 | Teague et al. |
| 8,091,182 B2 | 1/2012 | Hammerslag et al. |
| 8,597,222 B2 | 12/2013 | Lucero et al. |
| 2001/0008955 A1 | 7/2001 | Garth |
| 2002/0095750 A1 | 7/2002 | Hammerslag |
| 2003/0093882 A1 | 5/2003 | Gorza et al. |
| 2003/0204938 A1 | 11/2003 | Hammerslag |
| 2005/0081339 A1 | 4/2005 | Sakabayashi |
| 2005/0087115 A1* | 4/2005 | Martin ............... 114/39.19 |
| 2005/0160627 A1 | 7/2005 | Dalgaard et al. |
| 2005/0247813 A1 | 11/2005 | Kovacevich et al. |
| 2005/0273025 A1 | 12/2005 | Houser |
| 2006/0015980 A1 | 1/2006 | Nordt, III et al. |
| 2006/0015988 A1 | 1/2006 | Philpott et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0156517 A1 | 7/2006 | Hammerslag et al. |
| 2006/0185357 A1 | 8/2006 | Kovacevich et al. |
| 2006/0202077 A1 | 9/2006 | Kovacevich et al. |
| 2006/0202078 A1 | 9/2006 | Kovacevich et al. |
| 2007/0039085 A1 | 2/2007 | Kovacevich et al. |
| 2007/0169378 A1 | 7/2007 | Sodeberg et al. |
| 2008/0034459 A1 | 2/2008 | Nordt, III et al. |
| 2008/0039757 A1 | 2/2008 | Nordt, III et al. |
| 2008/0039764 A1 | 2/2008 | Nordt, III et al. |
| 2008/0039765 A1 | 2/2008 | Nordt, III et al. |
| 2008/0039767 A1 | 2/2008 | Nordt, III et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0083135 A1 | 4/2008 | Hammerslag et al. |
| 2008/0091132 A1 | 4/2008 | Bonutti |
| 2008/0319362 A1 | 12/2008 | Joseph |
| 2009/0030353 A1 | 1/2009 | Bonutti et al. |
| 2009/0287128 A1 | 11/2009 | Ingimundarson et al. |

(56) References Cited

U.S. PATENT DOCUMENTS

| | | |
|---|---|---|
| 2010/0139057 A1 | 6/2010 | Soderberg et al. |
| 2010/0168630 A1 | 7/2010 | Cropper et al. |
| 2010/0175163 A1* | 7/2010 | Litke .................. 2/161.4 |
| 2010/0217167 A1 | 8/2010 | Ingimundarson et al. |
| 2010/0268139 A1 | 10/2010 | Garth |
| 2010/0274364 A1 | 10/2010 | Pacanowsky et al. |
| 2010/0299959 A1 | 12/2010 | Hammerslag et al. |
| 2011/0009793 A1 | 1/2011 | Lucero et al. |
| 2011/0046528 A1 | 2/2011 | Stevenson et al. |
| 2011/0082402 A1 | 4/2011 | Oddou et al. |
| 2011/0098618 A1 | 4/2011 | Fleming |
| 2011/0105971 A1 | 5/2011 | Ingimundarson et al. |
| 2011/0178448 A1 | 7/2011 | Einarsson |
| 2011/0184326 A1 | 7/2011 | Ingimundarson et al. |
| 2011/0266384 A1 | 11/2011 | Goodman et al. |
| 2012/0010547 A1 | 1/2012 | Hinds |
| 2012/0029404 A1 | 2/2012 | Weaver, II et al. |

FOREIGN PATENT DOCUMENTS

| | | |
|---|---|---|
| CH | 577 282 A5 | 11/1974 |
| CH | 612 076 A5 | 1/1977 |
| CH | 624 001 A5 | 12/1977 |
| DE | 2341658 | 8/1972 |
| DE | 38 22 113 A1 | 6/1988 |
| DE | 93 15 776.2 U1 | 10/1993 |
| DE | 295 03 552.8 U5 | 3/1995 |
| DE | 199 45 045 A1 | 9/1999 |
| DE | 10057286 A1 | 5/2002 |
| DE | 2025007124 U1 | 6/2005 |
| EP | 0201051 | 12/1986 |
| EP | 393 380 B1 | 3/1990 |
| EP | 589 232 B1 | 8/1993 |
| EP | 589 233 B1 | 8/1993 |
| EP | 651 954 B1 | 11/1993 |
| EP | 614 624 A1 | 12/1993 |
| EP | 614 625 A1 | 1/1994 |
| EP | 693 260 B1 | 7/1995 |
| EP | 1 236 412 A1 | 2/2002 |
| FR | 2177294 | 11/1973 |
| FR | 2399811 | 3/1979 |
| JP | 3031760 U | 9/1998 |
| JP | 2004-016732 | 1/2004 |
| JP | 2004-041666 | 2/2004 |
| WO | 95/03720 A2 | 2/1995 |
| WO | 97/03581 A1 | 2/1997 |
| WO | 00/53045 A1 | 9/2000 |
| WO | 2004/110197 A2 | 12/2004 |
| WO | 2007016983 | 2/2007 |
| WO | 2009068503 | 4/2009 |

* cited by examiner

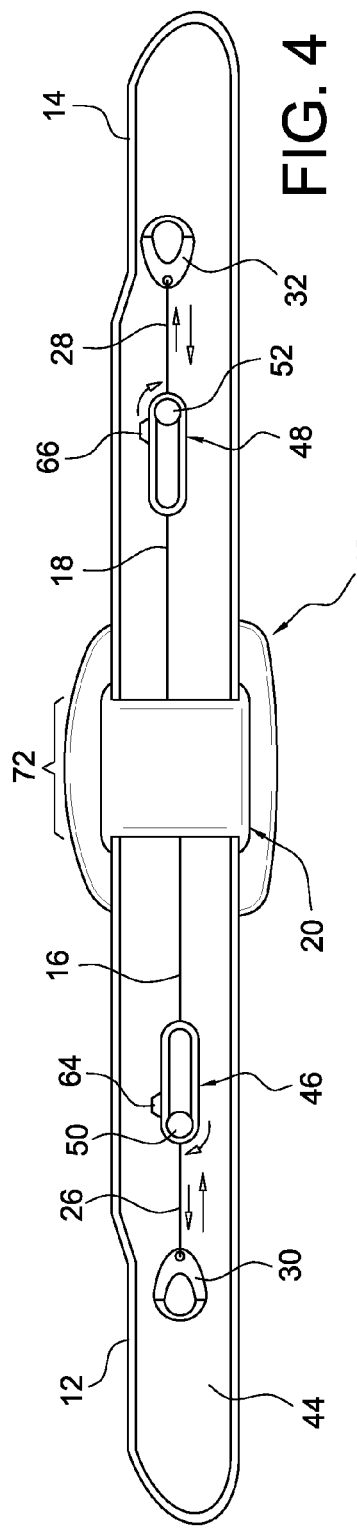

TIGHTENING SYSTEM FOR AN ORTHOPEDIC ARTICLE

CROSS-REFERENCE TO RELATED APPLICATIONS

This application claims the benefit of priority from U.S. provisional application No. 61/441,588, filed on Feb. 10, 2011, the entirety of which is incorporated by reference.

This application incorporates by reference the entirety of the following documents: U.S. patent application Ser. No. 12/713,268, filed on Feb. 26, 2010, U.S. patent application Ser. No. 12/938,593, filed on Nov. 3, 2010, U.S. patent application Ser. No. 12/466,597, filed on May 15, 2010, and U.S. Pat. No. 7,597,675, granted on Oct. 6, 2009.

FIELD OF ART

Embodiments of this disclosure are directed to tightening systems that incrementally adjust tension elements used alone or in combination in any variety of articles including orthopedics, prosthetics, bags, belts, sporting wear, footwear, clothing or other suitable articles.

BACKGROUND

There are numerous types of tightening systems for tensioning tension elements in or in combination with certain articles. Despite these known systems, there still exists a need for improving such systems.

For example, in the field of orthopedics, it is often desirable that an orthopedic article, such as in supports, braces, devices and other forms of wearable orthopedic items, is close-fitting in order to secure to and provide support for the wearer. As with many articles, orthopedic articles often rely on straps looped through buckles in order to secure to the wearer. Wearers may find difficultly in tightening such straps or other tension elements, such as laces or cords, used to secure these articles on the body due to friction between the strap and buckle or other tension elements, the location of such straps, a lack of mechanical advantage, or the inability to make minor adjustments in the tensioning without having to completely readjust the strap.

Some wearers may be infirm and lack the necessary strength to adequately secure the article onto their body. For example, patients with arthritic hands may lack the dexterity to securely grasp straps or buckles, and may also be unable to sufficiently pull the strap through buckles enough to firmly retain the article on the wearer. Various forms of tightening systems, for example hook and loop, buckles, and lacing, have been used to facilitate the closure and retention of known articles on the wearer. However, many of these known systems fail to permit adequate easy adjustment or the ability to slightly adjust the tightening of the article which leads to insufficient or excessive compression on the wearer.

In the example of an article in the form of a lumbar support, some known systems include the pulling of laces through a series of guide elements, for example pulleys, posts, rings or eyelets, so as to create a mechanical advantage. Yet many of these known systems suffer from the drawback of friction in the guide elements when the tensioning elements are adjusted. These systems are often limited in their mechanical advantage due to spacing and size constraints of the lumbar support itself.

With these known tightening systems in lumbar supports, multiple tension elements may be employed or require a relatively long distance to pull. This results in a significantly elongate tension element being wrapped about the torso of the wearer and affixed to the lumbar support. For those having reduced mobility or poor strength, such long travel required to properly tension the lumbar support may prove cumbersome. This also may result in the undesirable appearance of multiple tension elements being located on the surface of the lumbar support, which may also catch on items thereby causing safety concerns for the wearer of the support.

Although discussed in connection with orthopedic articles, many of the aforementioned issues with tightening systems may exist in applications outside of orthopedics as well, including but not limited to sporting wear, backpacks, belts, footwear, clothing or other suitable articles.

SUMMARY

The shortcomings in the prior art are overcome by the various tensioning system embodiments described herein. In accordance with this disclosure, the tightening system does not require the tension element to be pulled significantly far from a closure device, and can be selectively located about the surface of an article to provide an optimal location for the wearer. The embodiments of the tightening system can increase the mechanical advantage of a closure device, thereby further making it easier for a wearer to pull the tension element. Alternatively, the tightening systems may be employed without a closure device, of types known in the prior art and discussed herein. Moreover, the tightening system has a simple handle that can be selectively pulled in either short or long lengths according to the strength of the wearer in order to tighten the tightening system, with the option of releasing the handle at any point once the optimal tension is achieved which avoids the need from much manual dexterity. Additional means may be provided to finely adjust the tension element.

In accordance with one embodiment, the tightening system is for an article for a wearer, which may include any number of applications including orthopedics, sporting wear, footwear, clothing or other suitable articles. The tightening system includes a first member defining first and second ends, and a second member defining first and second ends. The first ends of the first and second members are spaced apart by a distance. A closure device connects the first and second members and includes a tension element. A tensioning mechanism is mounted on the first member and coupled to the closure device. The tensioning mechanism includes a housing and a retractable device having a retractable and extendable line arranged to be extended from the housing and automatically retracting to the housing upon release of the line to permit one-way incremental winding of the tension element to thereby draw the first and second members closer to one another by reducing the distance therebetween.

According to one variation, the retractable device includes a spring biased rotatable spool upon which the line is wound, a first rotatable spool upon which the line is wound, and a second rotatable spool upon which the tension element is wound. The first and second spools are rotatable in opposing directions. The retractable device may also have a release mechanism permitting unwinding of the tension element. A dosage meter may be connected to the tensioning mechanism, and indicate a tension level in the closure device.

In a variation, the tensioning mechanism may include a first gear device having a spring biased first spool secured to a second end of the line, and a first gear that engages the first spool and is rotatable therewith about a first axis. The first spool is lockingly rotatable with the first gear in a first rotational direction, and the first spool is freely rotatable relative to the first gear in a second rotational direction.

The tensioning mechanism may further include a second gear device having a second spool secured to a second gear and which are rotatable together about a second axis. The second gear device engages the first gear device in the first rotatable direction, and the first and second gears of the respective devices remain stationary when the first spool rotates in the second rotational direction. The tensioning mechanism further includes a release mechanism connected to the first gear device and is arranged to disengage the first gear device from the second gear device 3.

The tensioning mechanism preferably includes a handle secured to a first end of the line. The handle may be used to prevent the first end of the line from being fully retracted into the housing. Alternatively, at least part of the handle may be received by the housing or may attach to the housing.

The tensioning mechanism is selectively mountable over an outer surface of the first member at a plurality of locations. Another tensioning mechanism may be mounted onto the second member likewise at a plurality of locations.

The tightening system may have an intermediate member upon which the first end of at least one of the first and second members slides. The first and second members may be elongate and flexible, and releasably secure to one another at their second ends to define a belt or a strap.

In accordance with another embodiment, the tightening system has a rotary tensioning unit connected to the tensioning mechanism and permits fine tuning in tension of the tensioning mechanism in supplement to that obtained by pulling the handle and the line. The rotary tensioning unit is selectively engageable with the tensioning mechanism so as to be operative only when it is desired to supplement the tensioning obtained by the tensioning mechanism itself. The rotary tensioning unit may be spring loaded so as to only require small turning actions to provide additional tension in the tension element, rather than long turns of the rotary tensioning unit.

According to another embodiment for a tightening system, the tightening system includes a first member defining first and second ends, and a second member defining first and second ends. The first ends of the first and second members are spaced apart by a distance. A closure device connects the first and second members and includes a tension element. A rotary tightening device is mounted on the first member and engages the tension element. The rotary tightening device is arranged to permit one-way incremental winding of the tension element to thereby draw the first and second members closer to one another by reducing the distance.

The embodiment may include a handle extending from the rotary tightening device and coupled to the at least one tension element. The rotary tightening device is located between the handle and the first end of the first member. The handle is arranged to pull the at least one tension element so as to wind the tension element about the rotary tightening device, which tightens the tension element without adjusting the tension in the tension element between the handle and the rotary tightening device. The handle may be selectively positionable along an outer surface of the first member and relative to the rotary tensioning device.

In a method for tightening an article, the article has a first member defining first and second ends, a second member defining first and second ends such that the first ends of the first and second members are spaced apart by a distance, a closure device including a tension element and connecting the first and second members, and a tensioning mechanism mounted on the first member and coupled to the closure device. The tensioning mechanism includes a retractable and extendable line. The method includes the steps of: securing the first and second members at their second ends; pulling the line away from the housing to incrementally tighten the tension element and draw the first and second members closer to one another by reducing the distance; and releasing the line so as to retract to the housing without adjusting tension in the tension element. The method may further include the step of releasing tension in the tension element by releasing the tensioning mechanism from the tension element.

The numerous other advantages, features and functions of embodiments of the tightening system will become readily apparent and better understood in view of the following description and accompanying drawings. The following description is not intended to limit the scope of the tightening system, but instead merely provides exemplary embodiments for ease of understanding.

BRIEF DESCRIPTION OF THE DRAWINGS

FIG. 4 is a plan view showing a second embodiment of a tightening system in an orthopedic article of FIG. 1.

FIG. 5 is a plan view showing a third embodiment of a tightening system in an orthopedic article of FIG. 1.

FIG. 6 is a plan view showing a third embodiment of a tightening system in an orthopedic article of FIG. 1.

Figure 1:
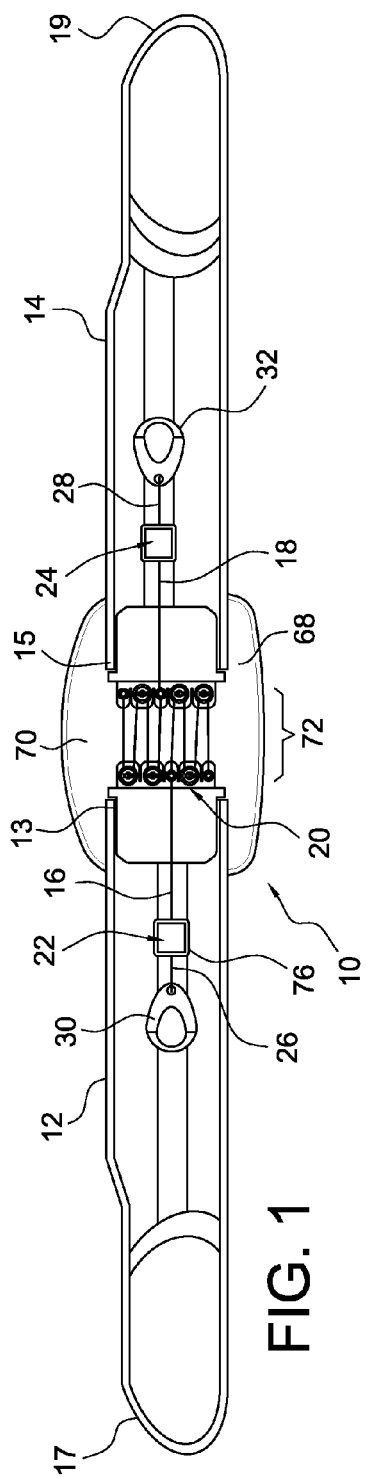
FIG. 1 is a plan view showing a tightening system in an orthopedic article defining a lumbar support.

In the various figures, similar elements are provided with similar reference numbers. It should be noted that the drawing figures are not necessarily drawn to scale, or proportion, but instead are drawn to provide a better understanding of the components thereof, and are not intended to be limiting in scope, but rather provide exemplary illustrations.

DETAILED DESCRIPTION OF VARIOUS EMBODIMENTS

While the tightening systems described herein may be used in a variety of articles, including orthopedics, prosthetics, harnesses, packs, sporting wear, footwear, clothing or other suitable articles, FIG. 1 depicts the tightening system in an orthopedic article 10. The exemplary orthopedic article is a lumbar support of a type more specifically described in U.S. patent application Ser. No. 12/713,268.

Figure 2:
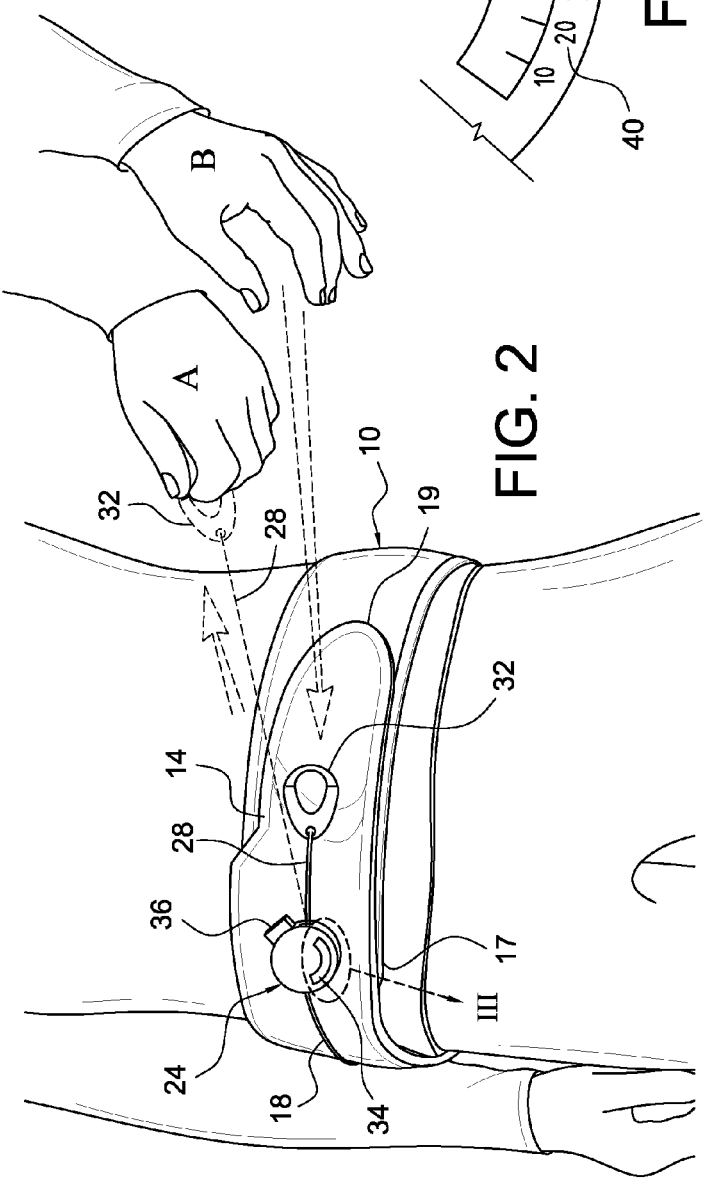
FIG. 2 is a schematic view showing the operation of the tensioning mechanism on the lumbar support according to FIG. 1.

As illustrated in FIGS. 1 and 2, the lumbar support 10 includes an intermediate member 70, such as a plate, first and second members 12, 14, in the exemplary form of elongate belt segments combining to form a belt, having first end portions 13, 15, and second end portions 17, 19. The first end portions 13, 15 are spaced apart by a variable distance 72, and the second end portions 17, 19 are securable to one another so as to form a belt. A closure device 20 couples the first end portions of the first and second members to the intermediate member 70. The closure device 20 is slidably mounted to the intermediate member 70 and arranged to move the first and second members 12, 14 relative to the intermediate member 70 between first and second linear directions, and adjust the length of the distance 72.

In a preferred embodiment, the closure device 20 includes a series of pulleys or other friction reducing means such as the type described in U.S. patent application Ser. No. 12/713,268. The closure device 20 preferably has a mechanical advantage of a four-to-one ratio, but can also be provided in variations of this preferred ratio.

The closure device 20 includes first and second tension elements 16, 18 having second ends connected to the series of pulleys. The first and second tension elements 16, 18 are arranged to move the first and second members 12, 14 relative to the intermediate member 70. The tension elements may be formed from any type of line, cord, strap, rope, string, wire, cable or other suitable element used to allow the user to apply tension.

A tensioning mechanism 22, 24 is mounted on the first and second members 12, 14, and connects to the closure device 20. The tensioning mechanism 22, 24 includes a housing 76 and a retractable device having a retractable and extendable line 26, 28.

As shown in FIG. 2, the line 28 is arranged to be extended from the housing 76 and automatically retracted to the housing 76 upon release of the line 28 to permit one-way incremental winding of the tension element 18 to thereby draw the first and second members 12, 14 closer to one another by reducing the distance 72.

The line may be formed from any type of strap, cord, rope, string, wire, cable or other suitable element used to allow the user to apply tension and retract into the housing. The line is capable of being drawn from the housing at a variety angles suitable to the wearer of the lumbar support, as shown in FIG. 2 and enabling tensioning of the tension element.

It will be noted that it is not necessary to provide two tensioning mechanisms, but that a single tensioning mechanism and tension element may be employed for the lumbar support. For example, the closure device may have only a single tension element as extending from the closure device for the lumbar support, and in turn a single tensioning mechanism is provided in combination with the tension element. On the other hand, the closure device may include two tension elements extending from one side of the closure device and corresponding to the first member, and a single tension element extends from the closure device on the side of the second member. Each tension element may be provided with one tensioning mechanism, or only the second member may be provided with a tensioning mechanism.

The tensioning mechanism 22, 24 preferably includes a handle 30, 32 secured to a first end of the line 26, 28. The handle 30, 32 is arranged to prevent the first end of the line from being retracted into the housing 76. The handle may selectively affix to the first and second members, or may freely extend from the tensioning mechanism when not used to tension the closure device.

The tensioning mechanism 22, 24 is preferably selectively mountable over an outer surface of the first and second members at a plurality of locations. For example, the handle may be locked relative to the tensioning mechanism and detached from the first member. The wearer pulls the handle thereby pulling the tension element and adjusting the closure device. Once a desired or near desired tension level is obtain, the wearer can mount the tensioning mechanism to the first member. The tensioning mechanism may have suitable hook and loop fastener elements that correspond to the surface of the first member so as to firmly affix the tensioning mechanism thereto. Of course, alternative fastening means may be employed to selectively affix the tensioning mechanism to the first member at a plurality of locations.

Alternatively, the tensioning mechanism may be permanently mounted on the first member, with an optimal location selected that permits easy access to the tensioning mechanism for adjustment of the lumbar support. In this instance, the adjustment is obtained solely from actuation of the tensioning mechanism which in turn adjusts the tension elements.

As depicted in the exemplary view of FIG. 2, the handle 32 may be mountable over the member 14 and the line 28 may have a specified, minimum length extending outwardly from the tensioning mechanism 24. As the handle 32 and line 28 are pulled outwardly relative to the tensioning mechanism 24, a portion of the tension element 18 is wound or retained within the tensioning mechanism 24. The handle can be appropriately sized to allow for a variety of hand sizes as well as levels of strength, as well as it can be made to be flexible or rigid. The handle in combination with the tensioning mechanism avoids the need for small devices that may have small dials or disks that are difficult to grasp and require some coordination and strength. This construction affords a system that allows for a variety of users to adjust tension settings by providing a simple and easy manner to do so.

After pulling the line 28 a certain distance up to its maximum length permitted by the line and subsequently releasing the handle 32, the tensioning mechanism 24 retracts the line 28 a specified distance into the closure device 24 so that the length of the line 28 extending outwardly from the housing returns to a minimum length while maintaining the portion of the tension element 18 wound in place in the tensioning mechanism 24.

If it is desired to additionally tension the tension element 18, the wearer may repeat the operation by pulling and retracting the line 28 repeatedly to incrementally tension and achieve the appropriate tension in the tension element 18, and thus the lumbar support over the torso of the wearer.

The tensioning mechanism 24 may include a dosage meter 34 having an indication feature, such as a scale 38 with indicia 40 that shows the tension in the tension element. An example of this could be achieved by providing a spring with a known force through the distance travelled to show on the scale the tension in the tension element. A release button 36 may be used to selectively and relieve the tension in the tension element maintained by the tensioning mechanism.

While a portion of the line is shown as extending away from the housing, it will be noted that the line may be fully retracted into the tensioning mechanism, such that there is no exposed length of the line when it is retracted, whereas only the handle extends from the tensioning mechanism. It follows that when tensioning the line, the handle is withdrawn from the tensioning mechanism and a portion of the line is exposed, but when the handle is released, the exposed length of the line is fully retracted into the tensioning mechanism.

This embodiment is particularly advantageous in that it provides a ratcheting system that can take advantage of a mechanical advantage in pulling the tension elements and tightening the same. Indeed, while the closure device itself has a mechanical advantage, the overall mechanical advantage of the tightening system may be further increased by the tensioning mechanism which itself may possess its own mechanical advantage.

The tightening system as a whole is advantageous in that it allows for a variety of wearer sizes since the line retracts; the tension element can be set to a specific length, and can accommodate different wearer sizes. For example, the minimum length of the line can be selected so that it could be used both on individuals with small girth or those with large girth; the length would be the same. Also, by reducing the minimum length of the tension element, there is less risk of exposure of the tension element and hence it catching on any objects.

FIG. 4 illustrates another embodiment 42 of the tightening system in a lumbar support. According to this embodiment, a rotary tightening device 50, 52 is provided in combination with the tensioning mechanism 46, 48. The rotary tightening device arranged to permit one-way incremental winding of the tension element 16, 18 to thereby draw the first and second members 12, 14 closer to one another by reducing the distance 72 between the first and second members in a finer manner than with the tensioning mechanism 46, 48. The rotary tightening device may be selectively engaged or disengaged with the tensioning mechanism by a bypass switch 64, 66.

FIG. 5 illustrates another embodiment 54 of the tightening system in a lumbar support. In this embodiment, a rotary tightening device 50, 52 is provided in combination with the tension element 16, 18 so as to incrementally tension the tension element 16, 18. A bypass switch 64, 66 is provided to permit engagement of the tension element with the handle carrying the line 26, 28 that allows for coarser adjustment of the closure device 20 relative to the adjustment provided by the rotary tightening device 50, 52. In this embodiment, there is no retractable device, and therefore the handle can be pulled away from a base unit 56, 58 that carry the rotary tightening device 50, 52 and can be engaged with the rotary tightening device 50, 52 by the bypass switch 64, 66.

FIG. 6 illustrates another embodiment 74 of a tightening system in a lumbar support. According to this embodiment, a base unit 60, 62 is adjustably mounted on the member 12, 14, and carries a rotary tightening device 50, 52. There is preferably no tensioning mechanism or line extending therefrom. Tightening of the tension element is either obtained by pulling the base unit 60, 62 when detached from the member 12, 14 away from the closure device, affixing the base unit 56, 58 to the outer surface 44 of the member 12, 14, and then if desired, finely adjusting the rotary tightening device 50, 52 to further tension the tension element.

The rotary tightening device may be arranged for only one-way incremental adjustment in a first rotational direction and release to permit free movement in a second rotational direction, or two-way incremental adjustment in first and second directions. The rotary tightening device may include a rotary tensioning device described in U.S. application Ser. No. 12/466,597, or a commercial example as produced by Boa Technology, Inc. of Steamboat Springs, Colo., under exemplary product names including HIGH POWER REEL, Series 30, MID POWER REEL M1, and LOW POWER REEL L3.

In each of the embodiments described herein, the tightening mechanism is either formed to be flexible or semi-rigid to accommodate being worn on the body of the wearer through the article upon which it is placed. Alternatively or in addition, the tightening mechanism may be sized appropriately small so that its size and any rigidity can likewise accommodate the wearer.

In observing FIGS. 7-10, an embodiment of the tensioning mechanism 22 has a retractable device including a rotatable first spool 82 biased by a spring 84, such as a helical coil spring, upon which the line 26 is wound, and a first gear 86 associated with the spool and rotatable with the spool about a pin 80 located along a common axis. According to this embodiment, the spool 82 defines a plurality of flexible prongs 83 that engage a plurality of inner teeth 87 formed on an inner ring of the gear 86. The prongs 83 permit movement of the spool 82 in a first rotating direction relative to the gear 86 so as to rotate freely relative to the gear 86, and lock with the inner teeth 87 in a second rotating direction so as to rotate with the gear 86 in such direction.

A second rotatable spool 90 is provided upon which the tension element 16 is wound, and which is associated with a gear 92 which is rotatable with the spool 90 about a common axis 88. The first and second gears 86, 92 mesh with one another and are rotatable in opposing directions as the line 30 is withdrawn from the housing 76.

The housing defines slots 77, 89 that permit ingress and egress of the line and the tension element. A release mechanism 78 is shown as pull-out switch having flanges which can be pressed together and pulled outwardly from the housing 76 to allow for disengagement of the first gear 86 from the second gear 92. A shaft 79 of the release mechanism 78 is connected to the pin 80 which is secured to the first gear 86 and spool 82, and the shaft 79 can be pulled through opening 85 defined by the housing 76.

Figure 8:
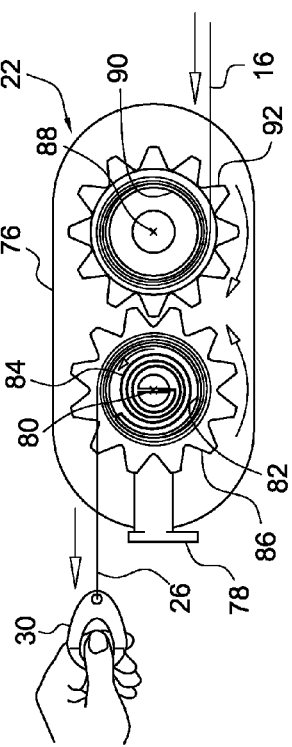
FIG. 8 is a schematic view showing the tensioning mechanism of FIG. 7 with a line drawn away therefrom.

As schematically shown in FIG. 8, the first and second gears 86, 92 engage with one another as the line 26 is pulled at the handle 30 from the housing. In doing so, the line 26 is unwound from the first spool 82, and the tension element 16 is wound about the second spool 90.

Figure 9:
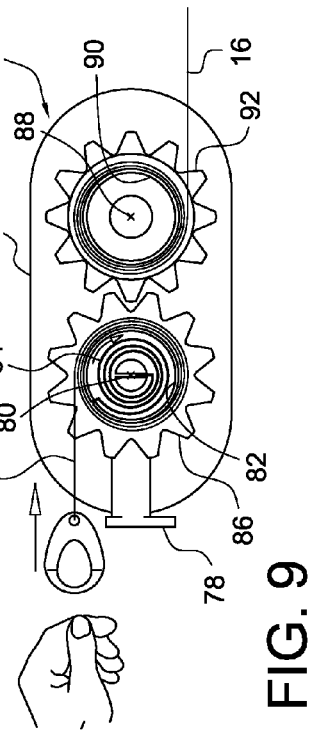
FIG. 9 is a schematic view showing the tensioning mechanism of FIG. 7 with retraction of the line.

Turning to FIG. 9 once the wearer either decides that additional tensioning is required or has reached a desire level, the handle 30 is released which then retracts to the housing 76 under the influence of the spring 84. In doing so, the line 26 is wound about the first spool 82, yet neither the first gear 86 nor the second gear 92 rotate, thereby locking the tension element 16 when the handle 30 was released.

Figure 10:
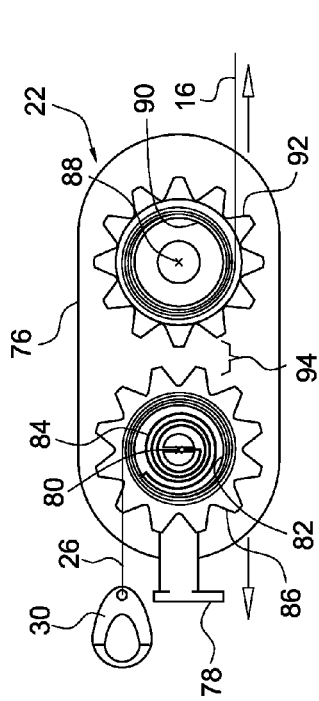
FIG. 10 is a schematic view showing the tensioning mechanism of FIG. 7 with disengagement of the tension element.

As shown in FIG. 10, when it is desired to release tension in the tension element 16, the wearer may pull the switch 78 outwardly from the housing 76 so as to disengage the first gear 86 from the second gear 92, and thereby allow the tension element 16 to relieve its tension that was obtained by pulling the line 26 in the step of FIG. 8.

Figure 11:
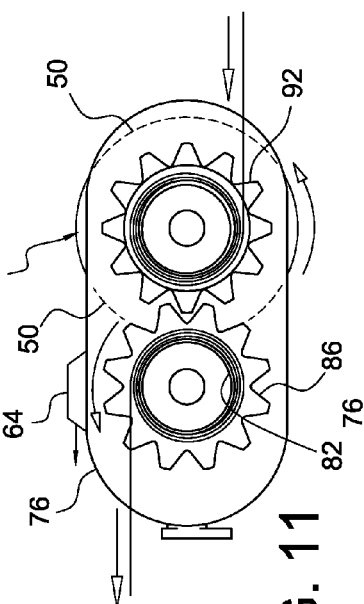
FIG. 11 is a schematic view showing a variation of the embodiment of FIG. 7 with a rotary tightening device.

In a variation of the tightening system, FIG. 11 generally shows the tensioning mechanism 46 corresponding to the embodiment of FIG. 4, wherein a rotary tightening device 50 may be associated with the second gear 92 so as to provide incremental fine adjustment of the tension element 16 which can be achieved by turning the rotary tightening device 50. In adjusting the tension element 16 by the rotary tightening device 46, the first spool 82 can be disengaged from the first gear 86 so the first and second gears 86, 92 can rotate freely without engagement of the first spool 82. Appropriate means, such as the switch 64, may be employed to disengage the first spool 82 from the first gear 86 such as by providing a button which causes the first spool 82 to disengage from the first gear 86.

Figure 12:
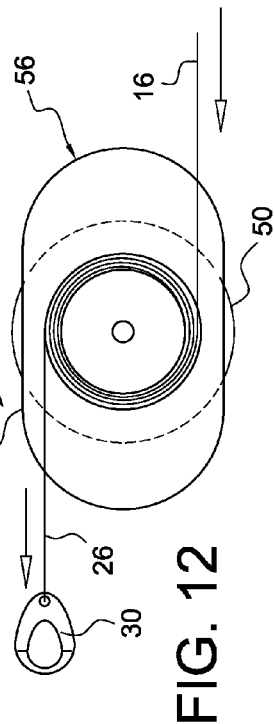
FIG. 12 is a schematic view showing another embodiment of a tensioning mechanism with a rotary tightening device connecting to a line with a handle.

In another variation of a tightening system, FIG. 12 generally shows the tensioning mechanism corresponding to the embodiment of FIG. 5, wherein a rotary tensioning mechanism 50 is used to finely adjust the tension element 16, and the line 26 can be pulled from the housing 76 to likewise tension the tension element 16.

Figure 13:
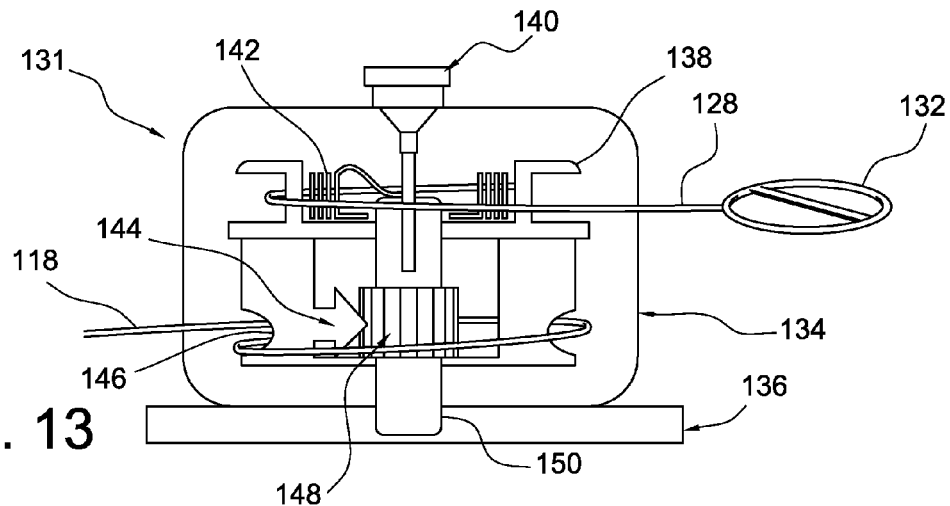
FIG. 13 is a sectional side view showing another embodiment of a tensioning mechanism.

FIG. 13 illustrates another embodiment of a tensioning mechanism 131. In this embodiment, the tensioning mechanism 131 has a housing 134 mounted on a base unit 136. An upper bobbin 138 is spring biased by a coil spring 142, and is used to retractably wind the line 128 connected to the handle 132. The tension element 118 winds about a lower bobbin 146 that engages a one-way rocker arm 144 and a one-way ratchet 148 located about a shaft 150. A release button 140 may be provided to release the upper bobbing 138 from the lower bobbin 146.

Figure 3:
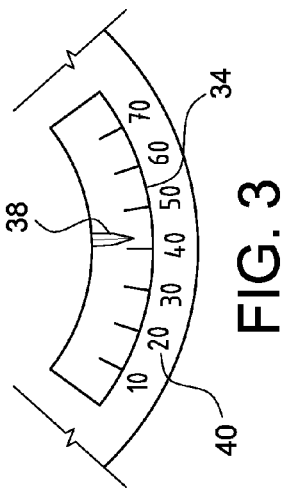
FIG. 3 is a sectional view showing a portion of the dosage meter depicted in FIG. 2.
Figure 7:
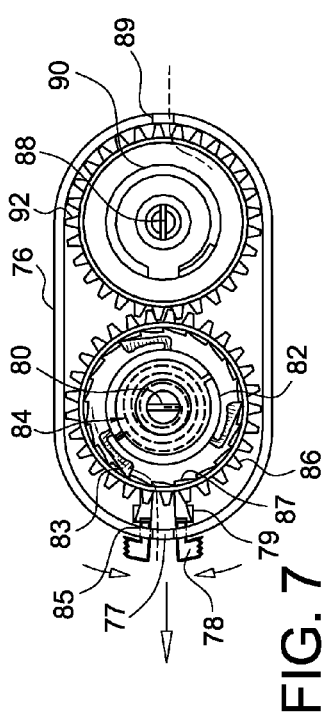
FIG. 7 is a plan view showing an embodiment of a tensioning mechanism.

The tensioning mechanism 131 operates in the same manner as described in connection to the embodiment of FIGS. 1-3, in that pulling the line 128 from the tensioning mechanism 131 incrementally draws the tension element 118 into the tensioning mechanism 131 by winding it about the lower bobbin 146.

Figure 14:
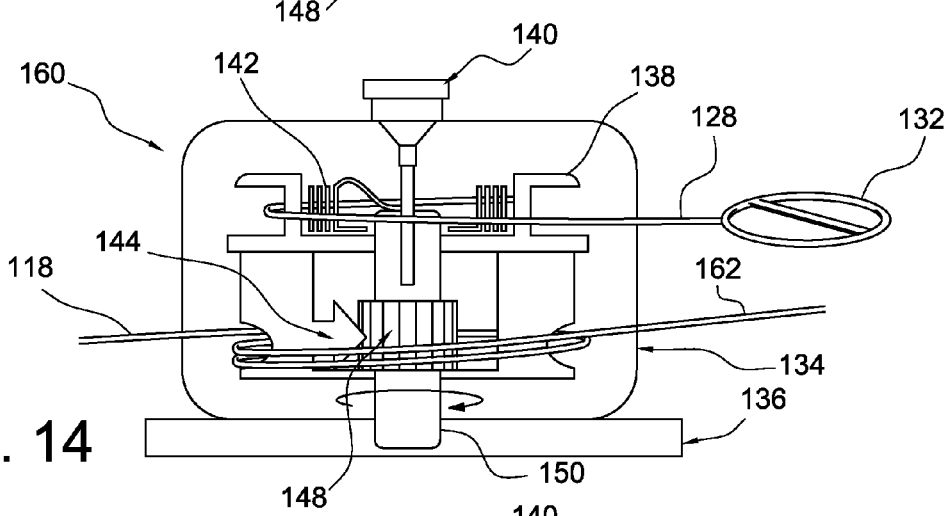
FIG. 14 is a sectional side view showing another embodiment of a tensioning mechanism.

FIG. 14 shows another embodiment wherein the tensioning mechanism 160 is a double acting retractable ratchet. According to this embodiment, the tensioning mechanism 160 winds two tension elements 118, 162 by a single pull of the line 128. In the example of the embodiment of FIGS. 1-3, the double acting tensioning mechanism 160 may replace the first and second tensioning mechanisms 22, 24 so that a single tensioning mechanism regulates the tension in both the tension elements 16, 18. This tensioning mechanism, for example, may be centrally located on an article so as to single handedly regulate two tension elements.

Figure 15:
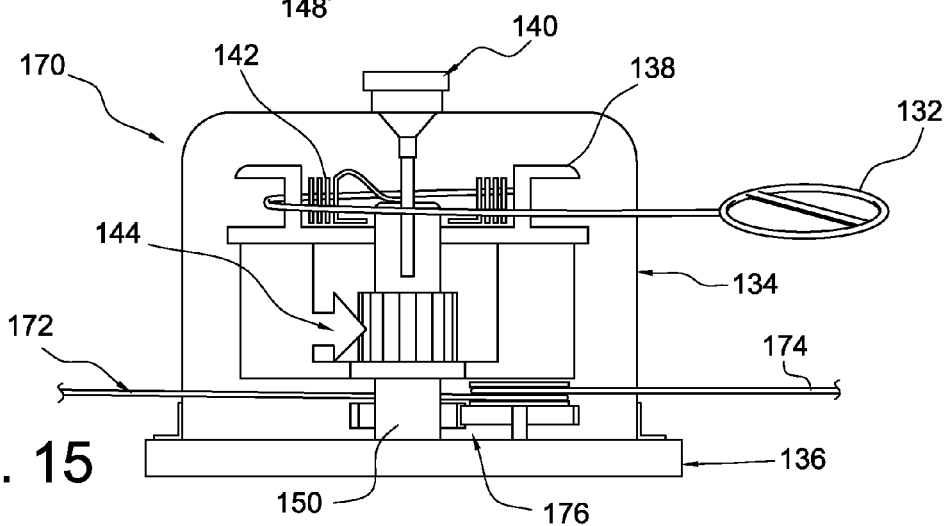
FIG. 15 is a sectional side view showing another embodiment of a tensioning mechanism.

FIG. 15 depicts another embodiment wherein the tensioning mechanism 170 is a double acting retractable ratchet having additional mechanical advantage and leverage. Specifically, the embodiment includes first and second tension elements 172, 174 that are wound about a reduction gear set 176. This embodiment may serve a similar purpose to the embodiment described in connection with FIG. 14.

While the foregoing embodiments have been described and shown, it is understood that alternatives and modifications of these embodiments, such as those suggested by others, may be made to fall within the scope of the invention. Moreover, any of the principles described herein may be extended to any other orthopedic devices or other types of articles devices requiring similar functions of those structural elements described herein.

The invention claimed is:

1. A lumbar support, comprising:
a first member arranged as a belt segment and defining first and second ends, the first member being elongate and flexible;
a second member arranged as a belt segment and defining first and second ends, the first ends of the first and second members being spaced apart by a variable distance, the second member being elongate and flexible;
a closure device spanning the variable distance, the closure device including a plurality of pulleys located on opposed sides of the first ends of the first and second members;
at least one tension element connecting the first and second members, a first end portion of the at least one tension element connecting to the plurality of pulleys;
a tensioning mechanism mounted on the first member and coupled to a second end portion of the at least one tension element, the tensioning mechanism including a housing and a retractable and extendable line arranged to be extended from the housing and automatically retract to the housing upon release of the line to permit one-way incremental winding of the at least one tension element to thereby draw the first and second members closer to one another by reducing said variable distance as the first end portion of the at least one tension element runs through the plurality of pulleys.

2. The lumbar support according to claim 1, wherein the tensioning mechanism has a retractable device including a spring biased rotatable spool upon which the line is wound.

3. The lumbar support according to claim 1, wherein the tensioning mechanism has a retractable device including a first rotatable spool upon which the line is wound, and a second rotatable spool upon which the at least one tension element is wound, the first and second spools rotatable in opposing directions and arranged along separate axes.

4. The lumbar support according to claim 1, wherein the tensioning mechanism has a retractable device including a release mechanism permitting unwinding of the at least one tension element through the plurality of pulleys without tensioning the line.

5. The lumbar support according to claim 1, further comprising a handle secured to a first end of the line and securable over the first member.

6. The lumbar support according to claim 5, wherein the handle extends a predetermined distance away from the housing when the line is fully retracted into the housing.

7. The lumbar support according to claim 1, further comprising a dosage meter connected to the tensioning mechanism, the dosage meter indicating a tension level in the at least one tension element.

8. The lumbar support according to claim 1, wherein the tensioning mechanism is selectively mountable over an outer surface of the first member at a plurality of locations.

9. The lumbar support according to claim 1, wherein the tensioning mechanism includes a first gear device having a first gear and a spring biased first spool secured to a second end of the line and engaging the first gear and rotatable therewith about a first axis, the first spool being lockingly rotatable with the first gear in a first rotational direction, and the first spool being freely rotatable relative to the first gear in a second rotational direction.

10. The lumbar support according to claim 9, wherein the tensioning mechanism further includes a second gear device having a second spool secured to a second gear and rotatable therewith about a second axis spaced away from the first axis, the second gear engaging the first gear in the first rotatable direction, the first and second gears remaining stationary when the first spool rotates in the second rotational direction.

11. The lumbar support according to claim 10, wherein the tensioning mechanism further includes a release mechanism connected to the first gear device and arranged to disengage the first gear device from the second gear device.

12. The lumbar support according to claim 1, further comprising an intermediate member upon which the first end of at least one of the first and second members slides.

13. The lumbar support according to claim 1, wherein the first and second members are elongate and flexible.

14. The lumbar support according to claim 13, wherein the first and second members releasably secure to one another at their second ends to define a belt with the closure device and the at least one tension element.

15. A tightening system comprising:
at least one tension element;
a tensioning mechanism coupled to the at least one tension element, the tensioning mechanism including a housing and a retractable device having a retractable and extendable line arranged to be extended from the housing and automatically retract to the housing upon release of the line to permit one-way incremental winding of the at least one tension element;

wherein the retractable device includes a release mechanism permitting unwinding of the at least one tension element from the tensioning mechanism;

wherein the tensioning mechanism includes a first gear device having a first gear and a spring biased first spool secured to a second end of the line and engaging the first gear and rotatable therewith about a first axis, the first spool being lockingly rotatable with the first gear in a first rotational direction, and the first spool being freely rotatable relative to the first gear in a second rotational direction;

wherein the tensioning mechanism further includes a second gear device having a second spool secured to a second gear and rotatable therewith about a second axis spaced away from the first axis, the second gear engaging the first gear in the first rotatable direction, the first and second gears remaining stationary when the first spool rotates in the second rotational direction.

16. The tightening system according to claim 15, further comprising a handle secured to a first end of the line, the handle preventing the first end of the line from being retracted into the housing.

17. The tightening system according to claim 16, wherein the handle extends a predetermined distance away from the housing when the line is fully retracted into the housing.

* * * * *